United States Patent [19]
Pon et al.

[11] Patent Number: 6,043,353
[45] Date of Patent: *Mar. 28, 2000

[54] REUSABLE SOLID SUPPORT FOR OLIGONUCLEOTIDE SYNTHESIS, PROCESS FOR PRODUCTION THEREOF AND PROCESS FOR USE THEREOF

[75] Inventors: Richard T. Pon; Shuyuan Yu, both of Calgary, Canada

[73] Assignee: University Technologies International, Inc., Canada

[*] Notice: This patent is subject to a terminal disclaimer.

[21] Appl. No.: 09/091,527

[22] PCT Filed: Dec. 13, 1996

[86] PCT No.: PCT/CA96/00836

§ 371 Date: Jun. 19, 1998

§ 102(e) Date: Jun. 19, 1998

[87] PCT Pub. No.: WO97/23496

PCT Pub. Date: Jul. 3, 1997

Related U.S. Application Data

[60] Provisional application No. 60/009,208, Dec. 22, 1995.
[51] Int. Cl.[7] .......................... C07H 21/00; C07H 21/02; C07H 21/04
[52] U.S. Cl. .................. 536/25.3; 536/25.33; 536/25.34
[58] Field of Search ................................ 536/25.3, 25.33, 536/25.34

[56] References Cited

U.S. PATENT DOCUMENTS

| | | | |
|---|---|---|---|
| 5,476,925 | 12/1995 | Letsinger ................................ | 536/23.1 |
| 5,736,626 | 4/1998 | Mullah et al. ........................... | 536/25.3 |
| 5,817,811 | 10/1998 | Breiphol et al. ......................... | 544/264 |

FOREIGN PATENT DOCUMENTS

| | | |
|---|---|---|
| 9603418 | 2/1996 | WIPO . |
| 9723497 | 7/1997 | WIPO . |

OTHER PUBLICATIONS

Uddin et al., "A Novel N[3]–Functionalized Thymidine Linker for the Stabilization of Triple Helical DNA," *J. Chem. Soc., Chem. Communications*, (Issue No. 2), 171–172 (Jan. 21, 1996).

Salord et al., "Targeting of Liposomes by Covalent Coupling with ecto–NAD[+]–Glycohydrolase Ligands," *Biochimica et Biophysica Acta*, 886(1), 64–75 (Apr. 8, 1986).

Pon et al.(I), "Hydroquinone–O,O'–Diacetic Acid as a More Labile Replacement for Succinic Acid Linkers in Solid–Phase Oligonucleotide Synthesis," *Tetrahedron Letters*, 38(19), 3327–3330 (May 12, 1997).

Pon et al.(II), "Rapid Automated Derivatization of Solid–Phase Supports for Oligonucleotide Synthesis Using Uronium or Phosphonium Coupling Reagents," *Tetrahedron Letters*, 38(19), 3331–3334 (May 12, 1997).

Cheruvallath et al., "Solution Phase Synthesis of an Oligodeoxyribonucleotide Phosphorothioate for Therapeutic Applications," *Nucleosides & Nucleotides*, 16(7–9), 1625–1628 (Jul.–Sep. 1997).

Krotz et al.(I), "Improved Impurity Profile of Phosphorothioate Oligonucleoitdes Through the Use of Dimeric Phosphoramidite Synthons," *Nucleosides & Nucleotides*, 16(7–9), 1637–1640 (Jul.–Sep. 1997).

Krotz et al. (II), "On the Formation on Longmers in Phosphorothioate Oligodeoxyribonucleotide Synthesis," *Tetrahedron Letters*, 38(22), 3875–3878 (Jun. 2, 1997).

Bulletin of the Chemical Society of Japan, vol. 60, No. 4, 1987, Tokyo, JP, pp. 1407–1413, XP000673487, J. Matsuzaki, et al.

Bioactive Molecules, vol. 3, 1987, pp. 4–21, XP000671967, M.H. Caruthers, et al.

*Primary Examiner*—W. Gary Jones
*Assistant Examiner*—L. E. Crane
*Attorney, Agent, or Firm*—Fitzpatrick, Cella, Harper & Scinto

[57] ABSTRACT

A solid support for oligonucleotide synthesis is disclosed. The solid support has formula (1) wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or different and are selected from the group consisting of —O—, —S—, —S(O)$_2$— and —N($R^{12}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; and Y is selected from the group consisting of: —CH$_2$—CH$_2$—; —CH$_2$—; —CH$_2$—O—CH$_2$—; —CH$_2$—CH$_2$—CH$_2$—; —CH=CH—; —CH=C(CH$_3$)—; —C(CH$_3$)=C(CH$_3$)—; —CH$_2$—C(=CH$_2$)—; and —CH$_2$—S—CH$_2$—; wherein when Y is —CH$_2$—CH$_2$—, at least one of $X^3$ and $X^4$ is —O—. An aspect of the invention also relates to a linker arm for oligonucleotide synthesis based on the solid support. Process for producing of the solid support and the linker arm, respectively, are also disclosed. The linker arm is characterized by being reusable in an otherwise conventional oligonucleotide production protocol.

40 Claims, 2 Drawing Sheets

REUSABLE SOLID SUPPORT FOR OLIGONUCLEOTIDE SYNTHESIS, PROCESS FOR PRODUCTION THEREOF AND PROCESS FOR USE THEREOF

This application claims priority to the U.S. Provisional Patent Appln. No. 60/009,208, filed Dec. 22, 1995.

TECHNICAL FIELD

In one of its aspects, the present invention relates to a reusable solid support for oligonucleotide synthesis. In another of its aspects, the present invention relates to a process for production of such a reusable solid support. In yet another of its aspects, the present invention relates to a process for use of such a reusable solid support.

BACKGROUND ART

The art of organic chemistry on solid supports is generally known. A useful review article on this topic may be found in "Organic Chemistry on Solid Supports" by Früchtel et al., *Angew. Chem. Int. Ed. Engl.,* 1996, 35, pgs. 17–42, the contents of which are hereby incorporated by reference.

As discussed in Früchtel et al., the art has developed automated solid-phase synthesis of polypeptides, oligonucleotides and oligosaccharaides. Of particular interest here is solid-phase synthesis of oligonucleotides. The following are useful review articles/textbooks on this topic:

Beaucage et al., *Tetrahedron,* 1992, 48, 2223;

Davis et al., *Innovation and Perspectives in Solid Phase Synthesis* (Ed.: R. Epton), Intercept, Andover, 1992, pg. 63;

Montserra et al., *Tetrahedron,* 1994, 50, 2617; and

S. L. Beaucage et al., *Tetrahedron,* 1993, 49, 6123–6194;

the contents of each of which are hereby incorporated by reference.

In the solid-phase synthesis of oligonucleotides, it is known to synthesize the oligonucleotide on an inorganic solid support bearing a succinyl linker arm—see, for example, any of the following references:

Caruthers et al., *Genetic Engineering,* Plenum Press, New York (1982), Vol. 4, pgs. 1–17;

Letsinger et al., *Genetic Engineering,* Plenum Press, New York (1985), Vol. 5, pg. 191;

Froehler et al., *Nucleic Acids Research,* 14:5399–5407 (1986); and

Matteucci et al., *Journal of American Chemical Society,* 103:3185–3186 (1981);

the contents of each of which are hereby incorporated by reference.

Typically, the succinyl linker arm has the following general formula:

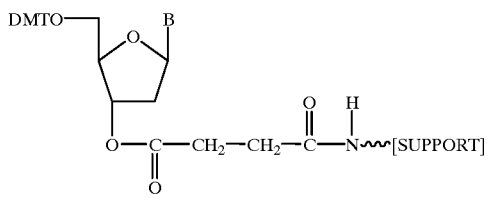

Thus, the succinyl group links the growing oligonucleotide from its terminal 3' hydroxyl group by an ester bond to a primary amine on the support, which may be, for example, conventional controlled pore glass (CPG) or silica, by an amide bond. Once the desired oligonucleotide has been synthesized, it is freed or cleaved from the succinyl linker arm hydrolyzing the ester carbonyl group. The hydrolysis agent is usually concentrated ammonium hydroxide. Typically, this reaction can take from 1–4 hours to complete. With improvements to current solid-phase oligonucleotide synthesizers, this cleavage step can represent 50% or more of the total time require to synthesize the desired oligonucleotide.

Another type of linker arm is disclosed in U.S. Pat. No. 5,112,962 [Letsinger et al. (Letsinger)], the contents of which are hereby incorporated by reference. Letsinger teaches a linker arm for solid support synthesis of oligonucleotides and oligonucleotide derivatives have the following formula:

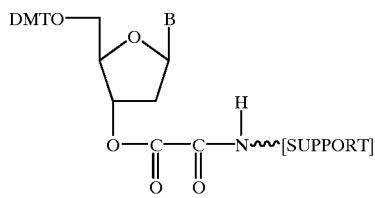

Thus, Letsinger teaches an oxalyl linker arm which purportedly release the synthesized oligonucleotide or oligonucleotide derivate in a period of 1–30 minutes in a manner that leaves the oligonucleotide fully protected. The oxalyl linker arm purportedly can be rapidly cleaved by 5% ammonium hydroxide in methanol, ammonium hydroxide, wet tertiary amine, triethylamine/alcohol, triethylamine/methanol, triethylamine/ethanol, aqueous trimethylamine and other bases. Unfortunately, the oxalyl linker arm of Letsinger suffers from its purported advantage. Specifically, the present inventors have discovered that the oxalyl linker arm of Letsinger is susceptible to significant spontaneous hydrolysis (e.g. spontaneous hydrolysis of ~10–40% per month) which renders it difficult to use in commercial operations. The oxalyl arm is also difficult to prepare because it requires using oxalyl chloride, which is highly reactive, toxic and therefore dangerous.

Regardless of the specific nature of the linker arm, it is generally accepted in the art that the linker arm is not reusable after production and cleavage of the desired oligonucleotide. Thus, conventional linker arms may be regarded as non-recyclable. This is illustrated in FIG. 1 which illustrates the conventional use of a succinyl linker arm for the production of an oligonucleotide. Thus, as illustrated, after cleavage of the desired oligonucleotide, the support is irreversibly linked to the linker compound (i.e. the succinyl moiety) and cannot be reused.

The art is in need of a linker arm for solid support oligonucleotide synthesis, which linker arm is recyclable. More specifically, the art is in need of a linker arm capable of repeated oligonucleotide synthesis/cleavage.

DISCLOSURE OF THE INVENTION

It is an object of the present invention to provide a novel solid support for oligonucleotide synthesis which obviates or mitigates at least one of the above-mentioned disadvantages of the prior art.

It is another object of the present invention to provide a novel process for producing the solid support.

It is an object of the present invention provide a novel linker arm for solid support oligonucleotide synthesis which obviates or mitigates at least one of the above-mentioned disadvantages of the prior art.

It is another object of the present invention to provide a novel process for producing a linker arm for solid support oligonucleotide synthesis.

Accordingly, in one of its aspects, the present invention provides a solid support for oligonucleotide synthesis, the solid support having the following formula:

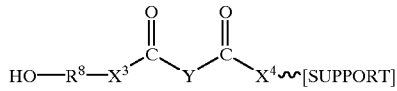

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or different and are selected from the group consisting of —O—, —S—, —S(O)$_2$— and —N($R^{12}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; and Y is selected from the group consisting of:

| | |
|---|---|
| —CH$_2$—CH$_2$—; | —CH$_2$—; |
| —CH$_2$—O—CH$_2$—; | —CH$_2$—CH$_2$—CH$_2$—; |
| —CH=CH—; | —CH=C(CH$_3$)—; |
| —C(CH$_3$)=C(CH$_3$)—; | —CH$_2$—C(=CH$_2$)—; and |
| —CH$_2$—S—CH$_2$—; | | wherein when Y is —CH$_2$—CH$_2$—, at least one of $X^3$ and $X^4$ is —O—.

In another of its aspects, the present invention provides a process for production of a solid support for oligonucleotide synthesis, the solid support having the following formula:

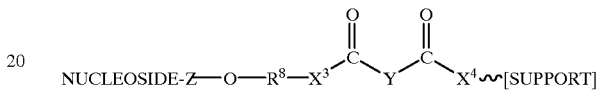

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or differed and are selected from the group consisting of —O—, —S—, —S(O)$_2$— and —N($R^{21}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; and Y is selected from the group consisting of:

| | |
|---|---|
| —CH$_2$—CH$_2$—; | —CH$_2$—; |
| —CH$_2$—O—CH$_2$—; | —CH$_2$—CH$_2$—CH$_2$—; |
| —CH=CH—; | —CH=C(CH$_3$)—; |
| —C(CH$_3$)=C(CH$_3$)—; | —CH$_2$—C(=CH$_2$)—; and |
| —CH$_2$—S—CH$_2$—; | | wherein when Y is —CH$_2$—CH$_2$—, at least one of $X^3$ and $X^4$ is —O—;

the process comprising the step of reacting together the compounds of Formulae I, II and III:

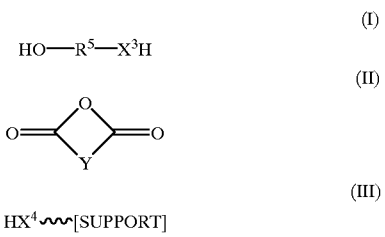

wherein $R^8$, $X^3$, $X^4$ and Y are as defined above.

In yet another of its aspects, the present invention provides a linker arm for solid support oligonucleotide synthesis, the linker arm comprising the following formula:

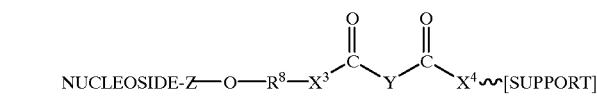

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or different and are selected from the group consisting of —O—, —S—, —S(O)$_2$— and —N($R^{12}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; Y is selected from the group consisting of:

| | |
|---|---|
| —CH$_2$—CH$_2$—; | —CH$_2$—; |
| —CH$_2$—O—CH$_2$—; | —CH$_2$—CH$_2$—CH$_2$—; |
| —CH=CH—; | —CH=C(CH$_3$)—; |
| —C(CH$_3$)=C(CH$_3$)—; | —CH$_2$—C(=CH$_2$)—; and |
| —CH$_2$—S—CH$_2$—; | | and Z is a linker moiety; wherein when Y is —CH$_2$—CH$_2$—, at least one of $X^3$ and $X^4$ is —O—.

In yet another of its aspects, the present invention provides a process for producing a linker arm for solid support oligonucleotide synthesis, the linker arm comprising the following formula:

NUCLEOSIDE-Z—O—$R^8$—$X^3$—C(O)—Y—C(O)—$X^4$—[SUPPORT]

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or different and are selected from the group consisting of —O—, —S—, —S(O)$_2$— and —N($R^{12}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; Y is selected from the group consisting of:

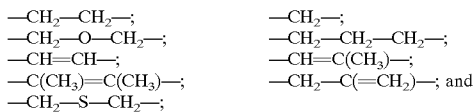

and Z is a linker moiety; wherein when Y is —CH$_2$—CH$_2$—, at least one of X$^3$ and X$^4$ is —O—;

the process comprising the step of reacting together the compounds of Formulae IV, V and VI: NUCLEOTIDE-OH (IV) HO—Z—OH (V)

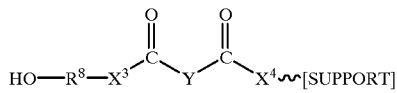

wherein R$^8$, X$^3$, X$^4$, Y and Z are as defined above.

As used throughout this specification, the term "oligonucleotide" is intended to have a broad meaning and encompasses conventional oligonucleotides, backbone-modified oligonucleotides (e.g. phosphorothioate, phosphorodithioate and methyl-phophonate analogs useful as oligotherapeutic agents) and oligonucleotide derivatives such as oligonucleotide-peptide conjugates.

Throughout this specification, when reference is made to a substituted moiety, the nature of the substitution is not specification restricted and may be selected from the group consisting of a C$_1$–C$_{20}$ alkyl groups, a C$_5$–C$_{30}$ aryl group a C$_1$–C$_{40}$ alkaryl group.

BRIEF DESCRIPTION OF THE DRAWINGS

Embodiments of the present invention will be described with reference to the accompany drawing in which.

BEST MODE FOR CARRYING OUT THE INVENTION

Initially, to facilitate an understanding of the invention, reference will be made to FIG. 1, which illustrates a conventional process for solid support oligonucleotide synthesis.

Figure 1:
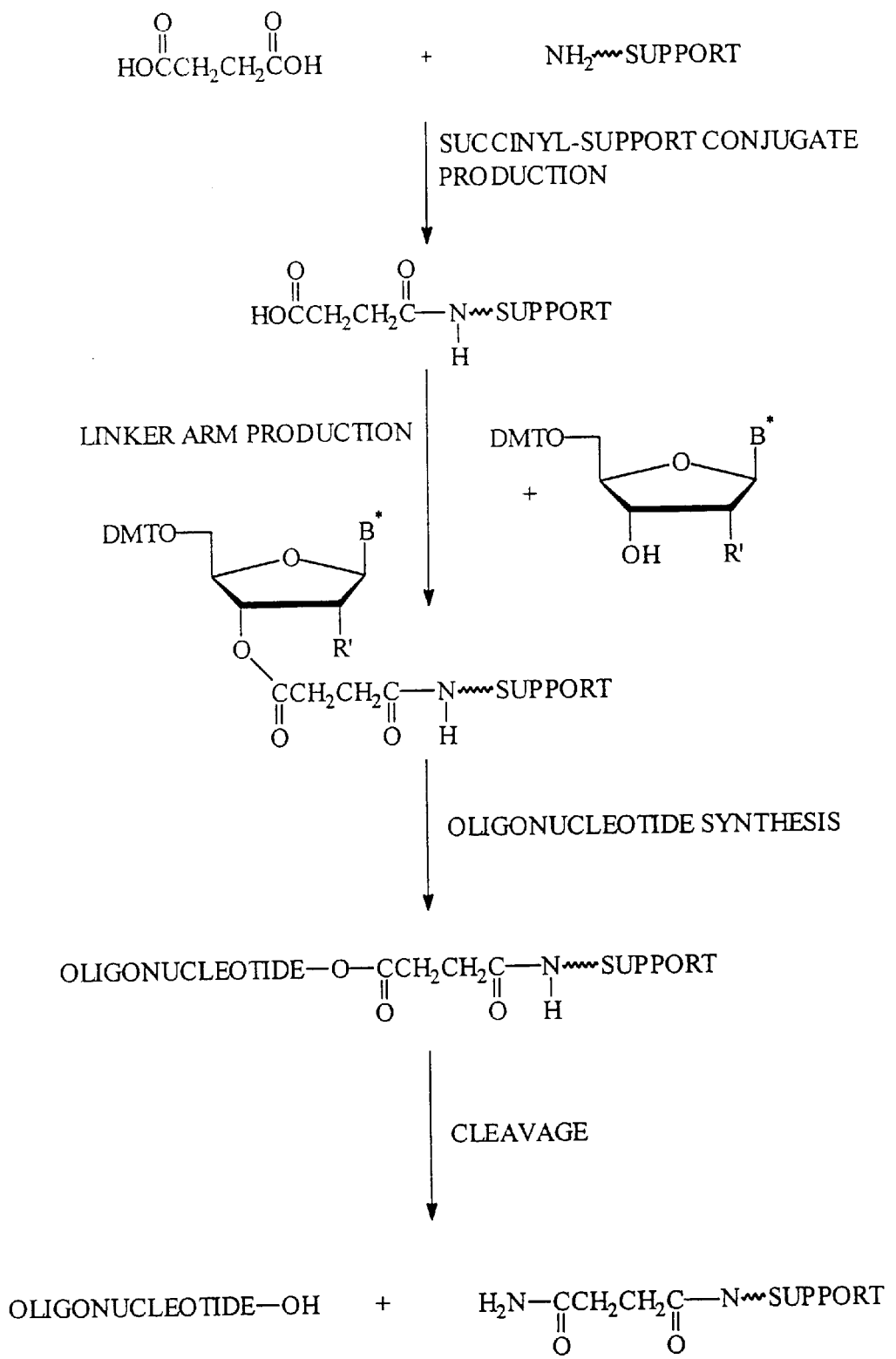
FIG. 1 illustrates a specific process pathway for conventional oligonucleotide synthesis.

Thus, the initial step of the process illustrated in FIG. 1 comprises reacting a linking compound, such as succinic acid (while succinic acid is illustrated, succinic anhydride may also be used), with a conventional amine-terminated support. The reaction results in the formation of an amide linkage between the linking compound and the support to produce succinyl-support conjugate.

Next, the succinyl-support conjugate is reacted with a desired initial nucleoside to produce a linker arm. In the illustrated nucleoside, DMT is dimethyoxytrityl, B is the nucleobase and R' is H (for deoxyribonucleosides) or OR (for ribonucleosides) wherein R is H or a conventional blocking/protecting group. The reaction results in the formation of an ester linkage between the linking compound and the desired initial nucleoside at the 3' position of the latter.

The linker arm is then used in conventional oligonucleotide synthesis (e.g. in a conventional automated synthesizer) to produce an oligonucleotide of desired sequence attached to the linker arm.

The oligonucleotide is then cleaved from the linker by hydrolysis. This serves to cleave the ester bond thereby freeing the oligonucleotide and an amine-terminated, non-reusable linker arm.

The present inventors have discovered that derivatization of a conventional support to provide a unique hydroxy-terminated functionality and then reacting this derivatized support with a conventional linking compound leads to production of a linker arm which may used to synthesize an oligonucleotide of desired sequence. A key feature of the invention is then the derivated support may be regenerated after cleavage of the oligonucleotide of desired sequence. To the inventors' knowledge, this is the first discovery of a derivatized support which may be used repeatedly in oligonucleotide synthesis.

The derivatized support of the present invention has the following formula:

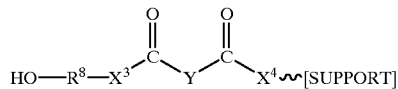

wherein: R$^8$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group; X$^3$ and X$^4$ are the same or different and are selected from the group consisting of —O—, —S—, —S(O)$_2$— and —N(R$^{21}$)—; R$^{12}$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group; and Y is selected from the group consisting of:

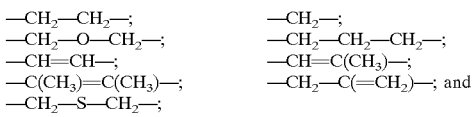

wherein when Y is —CH$_2$—CH$_2$—, at least one of X$^3$ and X$^4$ is —O—.

Preferably, R$^8$ is a substituted or unsubstituted C$_1$–C$_{20}$ alkyl group, more preferably a substituted or unsubstituted C$_1$–C$_{10}$ alkyl group, most preferably a member selected from the group consisting of ethyl, n-propyl, n-butyl, n-pentyl and n-hexyl. Preferably, R$^{12}$ is hydrogen.

Preferably, X$^3$ and X$^4$ are both —N(H)—. Also, preferably, Y is —CH$_2$—CH$_2$—.

The SUPPORT in the above formula is a conventional solid support. The nature of the solid support is not particularly restricted and is within the purview of a person skilled in the art. Thus, the solid support may be an inorganic substance. Non-limiting examples of suitable inorganic substances may be selected from the group consisting of silica, porous glass, aluminosilicates, borosilicates, metal oxides (e.g. aluminum oxide, iron oxide, nickel oxide) and clay containing one or more of these. Alternatively, the solid support may be an organic substance such as a cross-linked polymer. Non-limiting examples of a suitable cross-linked polymer may be selected from the group consisting of polyamide, polyether, polystyrene and mixtures thereof. The preferred solid support for use herein is conventional and may be selected from controlled pore glass bead or polystyrene beads.

The derivatized support of the present invention may be produced by a process comprising the step of reacting together compounds of the Formulae I, II and III:

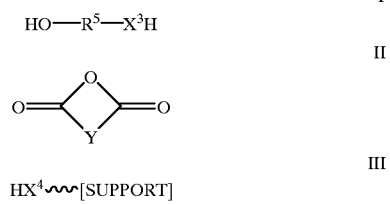

HO—$R^5$—$X^3$H    I

II

HX$^4$∼∼[SUPPORT]    III wherein $R^8$, $X^3$, $X^4$ and Y are as defined above. The discussion above with respect to preferred embodiments of $R^8$, $X^3$, $X^4$ and Y in the derivatized support applies equally here to the discussion of the process for producing the derivatized support.

The reaction of acid anhydride of Formula II with either the compound of Formula I or or the compound of Formula III needs no special activation. Attachment of the remaining compound to the combination of Formulae I and II, or Formula II and III, may be performed by activation of the carboxylic acid function by conventional means, for example by use of the activating agents discussed in more detail hereinbelow. Preferably, the compounds of Formulae II and III are combined first in the presence of a catalytic agent (e.g. 4-dimethylaminopyridine (DMAP)) in anhydrous pyridine. Then the compound of Formula I is attached using a carbodiimide reagent (e.g. 1-(3-dimethyl-aminopropyl)-ethylcarbodiimide (DEC)) and an acylation catalyst (e.g. DMAP) in an organic solvent (e.g. dichloromethane).

The derivatized supported may then be reacted with a conventional nucleoside-linker compound to produce the linker arm according to the present invention. This linker arm has the following formula:

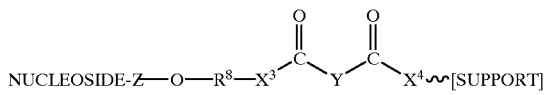

NUCLEOSIDE-Z—O—$R^8$—$X^3$   Y   $X^4$∼∼[SUPPORT]

wherein $R^8$, $X^3$, $X^4$ and Y are as defined above and Z is a linker moiety. The discussion above with respect to preferred embodiments of $R^8$, $X^3$, $X^4$ and Y in the derivatized support and process for production thereof applies equally here to the discussion of linker arm based on the derivatized support. Preferably, in the above formula, NUCLEOSIDE is a moiety selected from one of the following formulae:

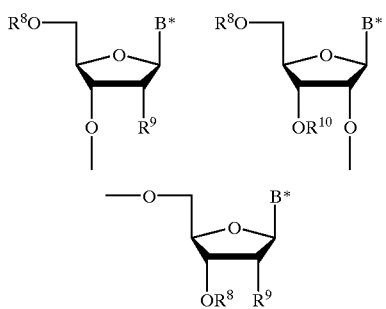

wherein $R^8$ and $R^{10}$ are the same or different and are hydrogen or a protecting group, $R^9$ is hydrogen (for deoxyribonucleosides or DNA) or —$OR^{11}$ (for ribonucleosides or RNA) wherein $R^{11}$ is hydrogen or a protecting group, and B* a nucleic acid base. Thus, in the case of RNA, there are two hydroxyl groups which may be protected. Also, the linker can be attached to either the 5'-, 3'- or (if ribose) 2'-hydroxyl positions. Indeed, for RNA sequences, it makes little difference whether the ester linker formed between the nucleoside and the linker compound is at the 2'- or 3'-hydroxyl position of the nucleoside. Thus, those of skill in the art will recognize that the nucleoside may be protected or blocked at the various of its hydroxyl moieties.

Non-limiting examples of useful protecting groups may be selected from the group consisting of trityl, methoxytrityl, dimethoxytrityl (DMT), dialkylphosphite, pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyldimethylsilyl, diisopropylmethylsilyl, diethylisopropylsilyl, triisopropylsilyl, acetyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, dimethoxybenzoin, dimethoxybenzoin carbonate, methylnitropiperonyl carbonate, fluorenyl-methoxycarbonyl, 2-phenylsulfonylethoxycarbony, fluorophenylmethoxypiperidinyl and the like.

As is known in the art, the main prerequisite for the protecting group used on the 5'-hydroxyl position is its ability to be selectively removed without causing cleavage of the linker arm. Thus, the preferred protecting group for desired 5'-hydroxyl position(s) is the acid labile dimethoxytrityl group. The main prerequisite for protecting groups on other hydroxyl positions, is stability to the conditions used for removal of the above protecting group. These latter protecting groups may be removed by the same conditions used to cleave the linker (discussed below) or separate conditions. The preferred protecting groups for these positions are trialkylsilyl (i.e. t-butyldimethylsilyl) or acetyl. Additional information may be obtained from the following references:

1. T. W. Greene and P. G. M. Nuts, "Protecting Groups in Organic Synthesis", Second Edition (1991), John Wiley and Sons, Inc., N.Y.;
2. M. Schelhaas and H. Waldman, "Protecting Group Strategies in Organic Synthesis", Angew. Chemie Int. Ed. Engl. 35, 2056–2083 (1996);
3. M. J. Gait, ed., "Oligonucleotide Synthesis A Practical Approach", IRL Press, Oxford (1984);
4. S. A. Narang, ed., "Synthesis and Applications of DNA and RNA", Academic Press, Inc., Orlando (1987); and
5. S. Agrawal, ed., "Methods in Molecular Biology, Vol. 20: Protocols for Oligonucleotides and Analogs", Humana Press, Totowa, N.J. (1993);

the contents of each of which are hereby incorporated by reference, for a discussion of other possible hydroxyl protecting groups.

The manner by which the desired nucleoside may be protected is conventional and within the purview of a person skilled in the art. See, for example U.S. Pat. No. 3,400,190 (Melby), U.S. Pat. No. 4,458,066 (Caruthers et al.), the contents of each of which are hereby incorporated by reference.

A preferred method for production of deoxyribonucleosides in the context of the present invention is to use a nucleoside with a 5'-dimethoxytrityl protecting group and an appropriate exocyclic amino protecting group, e.g., N$^6$-benzoyl-5'-dimethoxytrityl-2'-deoxyadenosine, N$^4$-benzoyl-5'-dimethoxytrityl-2'-deoxycytidine, 5'-dimethoxytrityl-N$^2$-isobutyryl-2'-deoxyguanosine, or 5'-dimethoxytritylthymidine.

A preferred method for production of ribonucleosides in the context of the present invention is to use a 5'-dimethoxytrityl protected nucleoside, with appropriate exocyclic amino protection, and no protecting groups on either of the 2'- or 3'-hydroxyl positions. The linker can then react with either one of the two adjacent hydroxyl groups (it doesn't matter which) to give a mixture of 2'- and 3'-linkages. The unreacted hydroxyl groups may then be acetylated by treatment of the immobilized nucleoside with acetic anhydride. Alternatively, ribonucleosides which have a 5'-dimethoxytrityl group, appropriate exocyclic amino group protection, and either a 3'-hydroxyl protecting group or a mixture of 2'- and 3'-protecting groups can be used. The 3'-protected compounds are generally unwanted isomers which are simultaneously produced when the 2'-hydroxyl position is protected and having little other use.

In the above formula for the present linker arm, Z is a linker moiety. As will be discussed below, Z is derived from a linker compound have the general formula HO—Z—OH (Formula V below). The nature of the linker compound is not particularly restricted.

In one preferred embodiment, linker moiety Z has the formula:

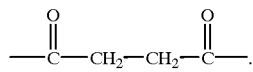

As will be apparent to those of skill in the art, this linker moiety may be derived from succinic acid or succinic anhydride.

In another preferred embodiment, linker moiety Z has the following formula:

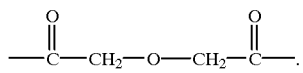

As will be apparent to those of skill in the art, this linker moiety may be derived from diglycolic acid or diglycolic anhydride.

In yet another preferred embodiment, linker moiety Z has the following formula:

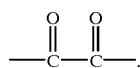

As will be apparent to those of skill in the art, this linker moiety may be derived from oxalic acid or oxalyl chloride.

In yet another, and most, preferred embodiment, linker moiety Z has the following formula:

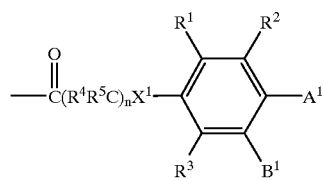

wherein: $R^1$, $R^2$ and $R^3$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $R^4$ and $R^5$ are the same or different and are selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^1$ is selected from the group consisting of —O—, —C(O)—, —S—, —S(O)$_2$— and —N(R)—; R is selected hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of $A^1$ and $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of $A^1$ and $B^1$ has the formula:

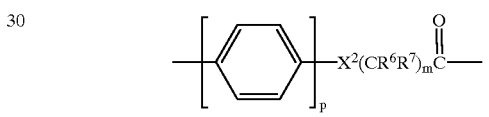

wherein p is 1 or 1, $X^2$ is selected from the group consisting of —O—, —S—, —C(O)—, —S(O)$_2$— and —N(R)—, R is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, $R^6$ and $R^7$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and m is 0, 1 or 2. In this embodiment, $B^1$ preferably is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group. Preferably, at least one, more preferably each, of R, $R^4$, $R^5$, $R^6$ and $R^7$ is hydrogen and preferably at least, more preferably both, of m and n are 1. It is further preferred that each of $R^1$, $R^2$ and $R^3$ is hydrogen and that $X^1$ and $X^2$ are both —O—. Thus, in this embodiment, the most preferred form of linker moiety Z is derived from hydroquinone-O,O'-diacetic acid.

In yet another preferred embodiment, linker moiety Z has the following formula:

wherein $R^4$, $R^5$, $R^6$ and $R^7$ are the same or different and are selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, Y is selected from the group consisting of O, S, $SO_2$ and O—$((CH_2)_L$—$O)_q$ 1 is an integer less than or equal to 60, q is an integer in the range of 1–1000, n and m are the same or different and are 1 or 2, with the proviso that, when Y is O, at least one of n and m is 2. Preferably, 1 is an integer in the range of 1–10, and q is an integer in the range of 1–1000. In this embodiment, the most preferred form of linker moiety Z is derived from thiodiglycolic acid (i.e. $R^4$=$R^5$=$R^6$=$R^7$=H, n=m=1 and Y=S).

The present linker arm may be produced by a process comprising the step of reacting together the compounds of Formulae IV, V and VI:

NUCLEOSIDE-OH     (IV)

HO—Z—OH     (V)

(VI)

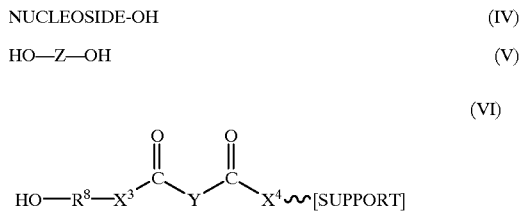

wherein $R^8$, $X^3$, $X^4$, Y and Z are as defined above. The discussion above with respect to preferred embodiments of $R^8$, $X^3$, $X^4$, Y and Z in respect of the linker arm of the present invention applies equally here to the discussion of the process to produce linker arm.

The compounds of Formulae IV, V and VI are preferably reacted in the presence of an activating agent. As used throughout this specification, the term "activating group" is intended to have a broad meaning and is intended to encompass electrophilic reagents capable of activating a carboxyl moiety (e.g on the linking compound of Formula V) by attachment of a leaving group to the acyl carbon of the carboxl moiety—see, for example, M. Bodanszky, "Principles of Peptide Synthesis", Second Edition, Springer-Verlag, Berlin (1993), the contents of which are hereby incorporated by reference. Thus, the activating agent should be capable of initiating at least one of the following: (a) formation of a reactive acylating agent (this is an example of a derivate) from the carboxyl moiety in a separate step or steps, followed by immediate treatment with the amino component (in this case, for example, an amino-terminated support) to form an amide linkage or a hydroxy component (in this case a hydroxy-terminated support or a hydroxyl group on the desired nucleoside) to form an ester linkage; (b) formation of an isolable acylating agent, separately, optionally with purification prior to treatment with the amino or hydroxy component as discussed in (a); and (c) formation of an acylating intermediate in the presence of the amino/hydroxy component, by the addition of an activating agent to a mixture of the two components. Thus, each of (a), (b) and (c) are applicable to the formation of both carboxylic esters and amides and all three routes can be used to attach nucleosides to supports.

For example, the Letsinger method, which first reacts oxalyl chloride with triazole, and then adds a nucleoside to the resulting oxalyl triazolide is an example of route (a). Conversion of the carboxylic acid group into an "active" ester using either p-nitrophenol, or di-, tri-, tetra-, or pentachlorinated or fluorinated phenols, or N-hydrosuccinimide are common examples of route (b). Route (c) has been the most commonly used method in recent years and both the carbodiimide reagents (dicyclohexylcarbodiimide, 1-(3-dimethylaminopropyl)-ethylcarbodiimide, and diisopropylcarbodiimide) and uronium reagents (O-(7-azabenzotriazol-1-yl)-1,1,3,3-tetramethyluronium hexafluorophosphate (HATU), 2-(1H-benzotriazol-1-yl)-1,1,3,3-tetramethyluronium hexafluorophosphate, (HBTU)) may be used in this approach.

In a preferred embodiment, in addition to an activating reagent, the reaction of the compounds of Formula (IV), (V) and (VI) is conducted in the presence of a nucleophilic catalyst or additive (typically 4-dimethylamino pyridine (DMAP), 1-hydroxybenzotriazole (HOBt), or 1-hydroxy-7-azabenzotriazole (HOAt)) to speed up the reaction and a tertiary amine base (typically triethylamine, pyridine, or diisopropylethylamine) to ionize the carboxylic acid group.

Thus, those of skill in the art will recognize that the precise nature of the activation agent is not particularly restricted provided, of course, that the activated carboxylic acid group is capable of initiating formation of the ester or amide linkage, as appropriate, and the activating reagent does not have any deleterious effect on the desired nucleoside.

Thus activation of the carboxylic acid by conversion into an acid chloride; an active ester (i.e. nitrophenyl, nitrophenylthio, trichlorophenyl, trifluorophenyl, pentachlorophenyl, pentafluorophenyl, or 3-hydroxy-2,3-dihydro-4-oxo-benzotriazine esters); an active hydroxylamine ester (i.e. N-hydroxyphthalimide or N-hydroxysuccinimide); acid anhydride; or mixed anhydride will produce derivates which will form the desired linkage, and thus, these strategies are encompassed herein.

Non-limiting examples of activating agents may be selected from the group consisting of arylsulfonyl chlorides (e.g. benzenesulfonyl chloride (BS-Cl), mesitylenesulfonyl chloride (MS-Cl), triisopropylsulfonylchloride (TPS-Cl)); active arylsulfonyl esters (i.e. imidazole, triazole, nitrotriazole, or tetrazole esters of BS-Cl, MS-Cl or TPS-Cl); 2-ethoxy-1-(ethoxycarbonyl)-1,2-dihydroquinoline (EEDQ); acyl carbonates; 1,1'-(carbonyldioxy) dibenzotriazoles; chlorotrimethyl-silane; carbodiimides (i.e. dicyclohexylcarbodiimide (DCC), 1-(3-dimethylaminopropyl)-ethylcarbodiimide (DEC), diisopropylcarbodiimide (DIC)) either alone or in combination with auxiliary nucleophiles (i.e. 1-hydroxybenzotriazole (HOBt), 1-hydroxy-7-azabenzotriazole (HOAt), N-hydroxysuccinimide (HOSu), or 3-hydroxy-3,4-dihydro-1,2,3-benzotriazin-4-one (HOObt)) and/or catalysts (i.e. 4-dimethylaminopyridine (DMAP) or N-methylimidazole (NMI)); or uronium salts (i.e. tetramethyluronium chloride (TMU-Cl), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1 (2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-dimethyleneuronium hexafluorophosphate (HAMDU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene) uronium hexafluorophosphate (HAPipU), O-(7-azabenzotriazol-1-yl)-1,1,3,3-bis(tetramethylene)uronium hexafluorophosphate (HAPyU), O-(7-azabenzotriazol-1-yl)-1,1,3,3-tetramethyluronium hexafluorophosphate (HATU)) either alone or in combination with auxiliary nucleophiles (i.e. 1-hydroxybenzotriazole (HOBt), 1-hydroxy-7- azabenzotriazole (HOAt), N-hydroxysuccinimide (HOSu), or 3-hydroxy-3,4-dihydro-1,2,3-benzotriazin-4-one (HOObt)) and/or catalysts (e.g. 4-dimethylaminopyridine (DMAP) or N-methylimidazole (NMI)) or phosphonium salts (e.g. benzotriazol-1-yl-oxytris(dimethylamino) phosphonium hexafluorophosphate (BOP), benzotriazole-1-yl-oxy-trispyrrolidinophosphonium hexafluorophosphate (PyBOP), 2-(benzotriazol-1-yl)oxy-1,3-dimethylimidazolidinium hexafluorophosphate (BOI), bromo tris(pyrrolidino)phosphonium hexafluorophosphate (PyBroP), 7-azabenzotriazol-1-yloxytris-(dimethylamino) phosphonium hexafluorophosphate (AOP), and 7-azabenzotriazol-1-yloxytris(pyrrolidino)phosphonium hexafluorophosphate (PyAOP)) either alone or in combination with auxiliary nucleophiles and/or catalysts (discussed above) will also produce the desired linkage.

Other examples of suitable activating reagents may be found in any of the following references:

M. Bodanszky, "Principles of Peptide Synthesis", Second Edition, Springer-Verlag, Berlin (1993);

J. Jones, "Amino Acid and Peptide Synthesis", Oxford University Press, Oxford (1992);

G. Grant, "Synthetic Peptides: A Users Guide", W. H. Freeman & Co., N.Y. (1992);

E. Haslam, Tetrahedron, 36, pg. 2409, (1980); and

M. A. Ogliaruso and J. F. Wolfe, "Synthesis of Carboxylic Acids, Esters and Their Derivatives", John Wiley & Sons, Chicester (1991);

the contents of each of which are hereby incorporated by reference.

In producing the present linker arm, the order of reaction is not particularly restricted. Thus, in one embodiment (this is the preferred embodiment), the compounds of Formulae IV and V are initially reacted to form a conjugate which is reacted with the compound of Formula VI. In another embodiment, the compounds of Formulae V and VI are initially reacted to form a conjugate which is reacted with the compound of Formula IV.

The addition of compounds of Formulae IV and V to Formula VI, usually will not result in the quantitative conversion of each immobilized hydroxyl group into a derivatized ligand. Therefore, it is preferred that unreacted hydroxyl groups on the surface of the support be protected (capped) by reaction with a capping reagent. This will mitigate the free hydroxyl group participating in subsequent oligonucleotide chain extension reactions, resulting in defect sequences lacking the terminal nucleoside. Preferably, the capping reagent should be reversible so that the capping agent can be removed to regenerate the hydroxyl sites prior to the next round of support derivatization. Capping of the unreacted sites is conventional and can be performed by reaction with an activated carboxylic acid or anhydride to form an ester, or by addition of a protecting group, as described hereinabove. Thus, for example, t-butylphenoxyacetic anhydride or preferably chloroacetic anhydride in 2,6-lutidine/THF solution combined with an equal volume of N-methylimidazole in THF solution are useful examples of capping reagents.

Figure 2:
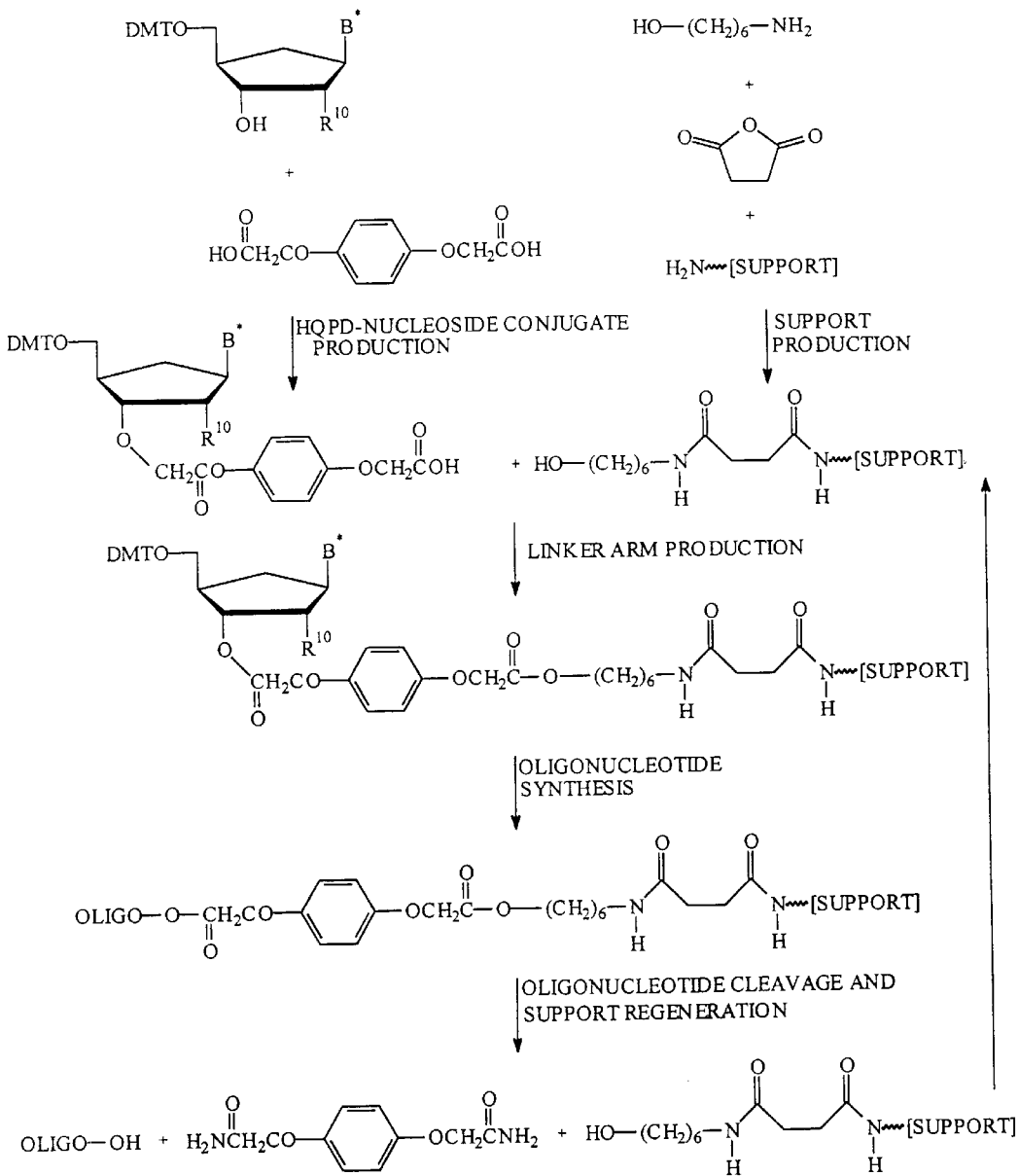
FIG. 2 illustrates a specific preferred embodiment of the present invention.

With reference to FIG. 2, there is illustrated a preferred reaction pathway for various embodiments of the invention. For clarity, the unreacted linker sites and the subsequent addition and removal of the capping groups is not shown in FIG. 2. In FIG. 2, DMT refers to dimethoxytrityl; B* refers to a nucleobase and $R^{10}$ is as described hereinabove. As will be apparent to those of skill in the art, the support is recycled after oligonucleotide cleavage and support regeneration to a point in the reaction scheme where it may again be coupled with the HQPD-nucleoside conjugate for further oligonucleotide synthesis.

With further reference to "oligonucleotide synthesis" in FIG. 2, once the present linker arm has been produced, it may be used in the conventional manner to synthesize an oligonucleotide—see, for example, U.S. Pat. No. 5,112,962 (Letsinger), incorporated by reference hereinabove. Once the oligonucleotide has been synthesized, it may be cleaved from the solid support to yield the free oligonucleotide and the support may then be regenerated—see FIG. 2.

The cleavage step comprises hydrolysis at the point of attachment of the initial nucleoside to the linking compound. The regeneration of the support involves the removal of two moieties: (i) the removal of the structure represented by Formula V (above) from Formula VI (above), which occurs simultaneously with the release of the oligonucleotide product, and (ii) the removal of the moiety used to protect (cap) unreacted hydroxyl sites of Formula VI (above) on the support. Removal of these two moieties can occur simultaneously or separately to regenerate the support. Simultaneous removal of both moieties using only a single reagent is simpler but care should be taken to use reagents which will not deleteriously affect the oligonucleotide product. A two-step regeneration involving the removal of the oligonucleotide using one reagent (typically ammonium hydroxide) and then treatment of the support with a second reagent (which may be faster but otherwise damaging to the oligonucleotide product thereby necessitating use of a two-step regeneration) allows flexibility in the choice of capping and regeneration reagents.

The reagent used to effect cleavage is not particularly restricted and is within the purview of a person skilled in the art. Preferably, the reagent is a base mild enough not to damage the oligonucleotide product but sufficiently strong to effect rapid cleavage. Non-limiting examples of suitable reagents for this purpose may be selected from the group consisting of ammonium hydroxide, ammonium hydroxide/methanol, ammonia/methanol, ammonium hydroxide/methylamine, potassium carbonate/methanol, t-butylamine, ethylenediamine, methylamine, dimethylamine, trimethylamine/water and the like. Cleavage may also be performed under neutral conditions using fluoride ion (i.e. 1M tetrabutylammonium fluoride/THF or triethylamine trihydrofluoride). The reagent used to remove the capping reagent from unreacted sites may consist of the above reagents or other stronger bases such as sodium or potassium hydroxide. In our preferred embodiment, ammonium hydroxide can be used to cleave the oligonucleotide product from the support, remove the HQPD linker arm, and cleave chloroacetyl protected hydroxyl groups in a single regeneration step. The preferred temperature for the cleavage and regeneration is room temperature, but higher or lower temperatures can be employed, subject to the limitations of the apparatus used.

Embodiments of the invention will be illustrated in the following Examples which should not be construed as limiting the scope of the invention. In the Examples, the following materials were used:

1. CPG, long chain alkylamine controlled pore glass, 120–200 mesh, 500 Å, 90–120 μmol/g of $NH_2$ groups), commercially available from CPG Inc. (Lincoln Park, N.J.);

2. HQPD, Hydroquinone-O,O'-diacetic acid, commercially available from Lancaster Synthesis Ltd. (Lancashire, England);

3. Ammonium hydroxide solutions (28–30%) and solvents were obtained from VWR Canlab (Edmonton, Alberta, Canada);

4. Cap A, a solution comprising acetic anhydride, 2,6-lutidine and tetrahydrofuran (THF) in a volume ratio of 1:1:8;
5. Cap B, a solution comprising N-methylimidazole and THF in a volume ratio of 16:84;
6. $I_2/H_2O$ oxidation, a solution comprising 0.05M $I_2$ in THF, $H_2O$ and pyridine in a volume ratio of 7:2:1;
7. Ammonium hydroxide/40% aqueous methylamine (AMA) in a volume ratio of 1:1;
8. Anhydrous pyridine and acetonitrile, distilled from $CaH_2$;
9. Anhydrous methanol, distilled from Mg turnings;
10. DIEA, diisopropylethylamine, reagent grade;
11. MeCN, acetonitrile, low water DNA synthesis grade;
12. DMAP, 4-dimethylaminopyridine, reagent grade;
13. DEC, 1-(3-dimethylaminopropyl)-ethylcarbodiimide, reagent grade;
14. HBTU, 2-(1H-benzotriazol-1-yl)-1,1,3,3-tetramethyluronium hexafluoro-phosphate, reagent grade;
15. HATU, O-(7-azabenzotriazol-1-yl)-1,1,3,3-tetramethyluronium hexafluorophosphate, reagent grade;
16. HOAT, 1-hydroxy-7-azabenzotriazole, reagent grade;
17. tBPA, t-butylphenoxyacetic anhydride in THF, obtained from Perseptive Biosystems;
18. HOBT, 1-hydroxybenzotrizole, reagent grade; and
19. TEA, triethylamine, reagent grade.

In the following Examples the amount of nucleoside (loading) on the insoluble supports was determined by spectrophotometric trityl analysis. In this procedure, a sample of support (4–5 mg) was accurately weighed directly into a 10 mL volumetric flask. A solution of dichloroacetic acid in 1,2-dichloroethane in a volume ration of 5:95 was then added to fill the flask. The contents were then thoroughly mixed and the absorbance of the orange coloured solution was measured at 503 nm using a Philips UV/V is spectrophotometer. The nucleoside loading (in $\mu$mol/g of CPG) was then calculated as:

Loading=$(A_{503} \times Vol \times 1000)/(Wt \times 76)$ wherein $A_{503}$=absorbance at 503 nm, Vol=solution volume in mL, and Wt=amount of CPG tested in mg. The accuracy of the trityl determination was approximately±2–3%.

EXAMPLES 1–5

Synthesis of 5'-dimethoxytritylnucleoside-3'-O-hemihydroquinone-O,O'-diacetates

Various HQPD-nucleoside conjugates were prepared using the following general technique:

HQPD (10 mmol, 2.26 g), 5'-dimethoxytrityl protected nucleoside (10 mmol), DMAP (1 mmol, 122 mg), DEC (10 mmol, 1.92 g), triethylamine (0.2 mL) and dichloromethane (50 mL) were combined in a 100 mL round bottomed flask and stirred at room temperature overnight. The solution was transferred to a separatory funnel, diluted with additional $CH_2Cl_2$ (50 mL), washed once with acidified $H_2O$ (150 mL $H_2O$ containing a few drops of 10% aqueous HCl) and several times with $H_2O$. The $CH_2Cl_2$ solution was dried over anhydrous $MgSO_4$, filtered, and then evaporated to yield the product as a light grey solid wherein B* and $R^9$ are as detailed in Table 1.

TABLE 1

| Example | B* | $R^9$ |
|---|---|---|
| 1 | $N^6$-benzoyladenine | H |
| 2 | $N^4$-benzoylcytosine | H |
| 3 | $N^2$-isobutyrylguanine | H |
| 4 | Thymine | H |
| 5 | Uracil | O-t-butyldimethylsilyl |

The crude material was checked by silica gel TLC (10% methanol/$CHCl_3$). The desired nucleoside-HQPD product was the major product (Rf≈0.04–0.13) with small amounts of starting 5'-dimethoxytrityl protected nucleoside (Rf≈0.4–0.7) and a byproduct, assumed to be the diester (Rf≈0.7–0.9). The crude material was suitable for attachment to the support and was used without further purification.

Thus, those of skill in the art will recognize that Examples 1–4 relate to the production of an HQPD-deoxyribonucleoside conjugate whereas Example 5 relates to the production of an HQPD-ribonucleoside conjugate.

EXAMPLE 6

Preparation of N-(1-hydroxyhexyl)-succinic diamide CPG

CPG (25 g), succinic anhydride (50 mmol, 5 g), DMAP (5 mmol, 610 mg) and anhydrous pyridine (110 mL) were combined in a 250 mL round bottom flask and shaken at room temperature (24 hours). The CPG was then filtered off, washed with methanol then chloroform, and dried.

Succinylated CPG (5 g), 6-amino-1-hexanol (1 mmol, 121 mg), DMAP (0.5 mmol, 61 mg), DEC (5 mmol, 958 mg), triethylamine (0.5 mL) and dichloromethane (20 mL) were combined in a 100 mL round bottom flask and shaken at room temperature overnight. Pentachlorophenol (2.5 mmol, 670 mg) was added and the flask was again shaken overnight. Piperidine (25 mL) was added and after shaking for 5 minutes, the CPG was filtered off, washed with methanol then chloroform and dried. To ensure quantitative blocking of all unreacted succinyl groups, the CPG was treated a second time with pentachlorophenol (2.5 mmol, 670 mg), DMAP (0.5 mmol, 61 mg), DEC (5 mmol, 958 mg), triethylamine (0.5 mL) and dichloroethane (20 mL). After shaking at room temperature overnight, piperidine (25 mL) was added and after another 5 minutes, the CPG was filtered off, washed as above and dried.

EXAMPLES 7–11

Coupling of HOPD-Nucleoside Conjugates to the N-(1-hydroxyhexyl)-Succinic Diamide CPG In Examples 7–11, the various HQPD-nucleoside conjugates produced in Examples 1–5, respectively, were coupled to the support produced in Example 6 to produce various linker arms within the scope of the present invention.

The following general procedure was used: hydroxyl derivatized CPG (250 mg), HBTU (0.05 mmol, 19 mg), HOBT (0.05 mmol, 7 mg), and HQPD-nucleoside conjugate (0.05 mmol) were combined in a 4 mL glass vial and sealed with a septum; DIEA (1.5 mmol, 0.26 mL) and anhydrous acetonitrile (1.3 mL) were added via syringe; the vial was shaken at room temperature for 10 minutes; then the CPG was filtered off, washed with dichloromethane and dried. The nucleoside loading was determined by colorimetric trityl analysis (R. T. Pon in "Methods in Molecular Biology", Vol. 20: Protocols for Oligonucleotides and Analogs, S. Agrawal, ed., 1993, Humana Press Inc., Totowa, N.J., the contents of which are hereby incorporated by reference) and are reported in Table 2.

TABLE 2

| Example | HQPD-nucleoside conjugate prepared in Example # | Nucleoside Loading ($\mu$mol/g) |
|---|---|---|
| 7 | 1 | 39.1 |
| 8 | 2 | 37.7 |
| 9 | 3 | 23.9 |
| 10 | 4 | 39.5 |
| 11 | 5 | 24.2 |

EXAMPLES 12–22

Automated Strategies For Coupling HOPD-Nucleoside Conjugates to the N-(1-Hydroxyhexyl)-Succinic Diamide CPG In these Examples, the methodology described in Examples 7–11 was employed using a Perkin-Elmer Applied Biosystems 394 automated DNA synthesizer. The HQPD-nucleoside conjugate (0.2 M, 1 eq.) with DIEA (2 eq.) and the coupling agent (0.2 M), both in filtered acetonitrile solution, were respectively installed on bottle positions #7 and #8 of the automated synthesizer. Hydroxyl derivatized CPG (prepared in Example 6) was placed into a plastic synthesis column (~12 mg/column) and installed on column position #1 of the synthesizer. A custom program (begin procedure) was prepared which: (i) washed the column with acetonitrile (4×20 sec); (ii) simultaneously delivered solutions from both bottle positions #7 and #8 to fill the synthesis column (4.0 sec); (iii) waited a variable amount of time (0–600 sec) to allow the coupling reaction to procede; and (iv) washed the column clean with acetonitrile (4×20 sec). The amount of nucleoside loading was determined by calorimetric analysis of the trityl colours released by the synthesizer using an unmodified synthesis cycle. The above procedure was used to evaluate the extent and rate of a number of different coupling agents and the results are reported in Table 3.

EXAMPLE 23
Support Recyclability I

In this Example, an initial study was conducted to determine the ability to conduct multiple cycles of nucleoside coupling (as described in Examples 7–11) and cleavage of the HQPD linker using the support described in Example 6.

The equipment used in this Example was a model 394 DNA synthesizer commercially available from Perkin-Elmer, Applied Biosystems Division. The synthesizer was custom programmed to achieve simultaneous mixing of a solution (0.2 M) of HQPD-nucleoside conjugate and DIEA (0.4 M) in anhydrous acetonitrile with a solution (0.2 M) of HBTU/HOBT/DIEA in anhydrous acetonitrile followed by a ten minute coupling (wait) step as described in Examples 12–22. Further, the synthesizer was operated to employ a 10 minute cleavage step using an AMA solution with no capping steps.

The nucleoside loading levels on the support for successive cycles of coupling and cleavage using the same HQPD-nucleoside conjugate are reported in Table 4. For clarity, in Table 4, reference is made to Examples 1–4 above for the particular HQPD-nucleoside conjugate used.

TABLE 3

| | | | | Nucleoside Loading Level ($\mu$mol/g) | | | | |
|---|---|---|---|---|---|---|---|---|
| Example | B* | $R^9$ | Coupling Agent[1] | 0 sec[3] | 60 sec[3] | 150 sec[3] | 300 sec[3] | 600 sec[3] |
| 12 | T | H | HBTU (alone) | — | 14.6 | — | 35.3 | 47.1 |
| 13 | T | H | HBTU/HOBT[2] | — | — | — | — | 57.7 |
| 14 | T | H | HBTU/DMAP (1:0.05) | — | 28.2 | 41.6 | 53.0 | 63.4 |
| 15 | T | H | HBTU/DMAP | — | 60.1 | 66.0 | 67.2 | 72.2 |
| 16 | $G^{ibu}$ | H | HBTU/NMI | — | 12.5 | — | 32.7 | 35.3 |
| 17 | $G^{ibu}$ | H | HBTU/HOBT[2] | — | 22.0 | — | 32.2 | 32.3 |
| 18 | $G^{ibu}$ | H | HBTU/DMAP | — | 34.1 | 33.2 | 32.9 | 32.3 |
| 19 | T | H | HBTU/DMAP | 26.6 | 58.7 | — | — | — |
| 20 | T | H | HATU/HOAT[2] | — | 19.9 | 29.6 | 41.8 | 50.0 |
| 21 | T | H | HATU/DMAP | 44.0 | 63.2 | 67.0 | — | — |
| 22 | T | H | HATU/NMI | 8.6 | 23.1 | — | 37.4 | 43.9 |

Notes:
[1]unless otherwise indicated all reagents are in a 1:1 molar ratio
[2]also includes one equivalent of DIEA.
[3]wait step

TABLE 4

| | Nucleoside Loading Level Using HQPD-Nucleoside Conjugates ($\mu$mol/g) | | | |
|---|---|---|---|---|
| Cycle # | Example 1 | Example 2 | Example 3 | Example 4 |
| 1 | 50.4 | 47.5 | 35.2 | 33.6 |
| 2 | 41.2 | 42.1 | 30.1 | 37.3 |
| 3 | 38.2 | 38.5 | 35.3 | 32.5 |
| 4 | 35.1 | 40.4 | 30.2 | 39.7 |
| 5 | 36.2 | 39.7 | 29.0 | 29.6 |
| 6 | 35.4 | 37.5 | 32.0 | — |
| Average | 39.4 | 41.0 | 32.0 | 34.5 |

The results reported in Table 4 clearly show that, at least in regard to the initial nucleoside coupled to the support, it is possible to repeatedly cleave off the nucleoside and couple it again to the support in the form of an HQPD-nucleoside conjugate.

EXAMPLE 24

Support Recyclability II

In this Example, multiple oligonucleotides were produced using the DNA synthesizer described in Example 23 and the linker arm produced in Example 10 above.

Initially, the linker arm was capped with a mixture of tBPA solution and Cap B reagent (1:1 by volume) for 30 minutes and then packed into three plastic synthesis columns (40–60 mg of support/column). Multiple synthesis columns were used to mitigate any difficulties which might be encountered in manipulating small amounts of the linker arm through the various steps. The synthesis columns were used in parallel on the DNA synthesizer with an unmodified 1 μmol scale synthesis program to prepare a 17-base oligonucleotide.

After synthesis of the desired oligonucleotide, the DNA synthesizer automatically attended to cleavage thereof by contacting the support with ammonium hydroxide for a period of 3 minutes. The oligonucleotide product in ammonium hydroxide solution was removed for analysis and then the synthesis columns were removed and disassembled. The spent linker arm material from each column was combined and then regenerated by stirring in a solution of AMA for a period of 30 minutes. The cleavage regeneration was done using this two step procedure to avoid exposing the oligonucleotide to the AMA solution. The regenerated support was dried under vacuum and the coupling, capping, oligonucleotide synthesis, cleavage and linker arm regeneration steps were repeated cyclically.

The specific nucleoside loading level obtained from the coupling step (N.L.), the average yield for each of the chain extension steps during the oligonucleotide synthesis (A.Y.), the amount of linker arm used (L.A. Amt.), the oligonucleotide sequence synthesized, and the amount of crude oligonucleotide (Oligo. Yield) produced are reported in Table 5.

As illustrated in Table 5, the present linker arm is capable of being used in cycle steps of: (i) coupling (i.e. to produce the linker arm), (ii) capping, (iii), oligonucleotide synthesis, (iv) oligonucleotide cleavage, and (v) linker arm regeneration.

EXAMPLE 25

Support Recyclability III

The methodology of Example 16 was repeated except that the duration of the coupling, capping, and regeneration steps was reduced to 10 minutes.

In this Example, six oligonucleotides were successively produced using the same support material. The various process parameters and product properties reported in Example 24 are reported for this Example in Table 6.

EXAMPLE 26

Support Recyclability IV

In this Example, all the steps involved in a cycle of coupling, capping, oligonucleotide synthesis, cleavage and regeneration were performed by the automated DNA synthesizer to eliminate any manual handling of the solid-phase support.

An 11.8 mg sample of the support prepared in Example 6 was packed into a single plastic synthesis column. Coupling of HQPD-nucleoside conjugates, as prepared in Examples 1–4, was performed in a similar manner as Example 15 using a 150 second coupling time and was followed by a 5 minute capping step using equal volumes of 0.5 M chloroacetic anhydride/2, 6-lutidine in THF and Cap B reagent. The chloroacetic anhydride solution also replaced the Cap A reagent (acetic anhydride) normally used during the oligonucleotide synthesis steps. Otherwise, an unmodified 0.2 μmol scale synthesis cycle was used for the oligonucleotide synthesis. Cleavage of the oligonucleotide and regeneration of the support was performed simultaneously with a ten minute treatment with ammonium hydroxide (no AMA solution was required). The relevant process parameters and product properties are reported in Table 7.

EXAMPLES 27–39

Use of 5'-dimethoxytrityl-2'-deoxyribonucleoside-3'-O-hemisuccinates

In the following Examples, the commercially available nucleosides: $N^6$-benzoyl-5'-dimethoxytrityl-2'-deoxyadenosine-3'-O-hemisuccinate; $N^4$-benzoyl-5'-dimethoxytrityl-2'-deoxycytidine-3'-O-hemisuccinate; 5'-dimethoxytrityl-$N^2$-isobutyryl-2'-deoxyguanosine-3'-O-hemisuccinate; and 5'-dimethoxytritylthymidine-3'-O-hemisuccinate were evaluated in procedures similar to those outlined in Examples 12, 15, 20 and 21 above. However, in the following Examples, reagent concentrations of either 0.05M or 0.2M were evaluated. Also, because of limited solubility, the 5'-dimethoxytritylthymidine-3'-O-hemisuccinate was dissolved in 1:1 (by volume) dichloromethane:acetonitrile instead of just acetonitrile. The results are reported in Table 8.

The results in Table 8 indicate that nucleosides containing a succinic acid moiety couple less effectively than nucleosides containing an HQPD moiety (e.g. compare Examples 13 and 17 with Example 31) when using the HBTU/HOBT reagent. However, use of HBTU/DMAP or the even more powerful HATU/DMAP reagent can still provide rapid and satisfactory nucleoside loading levels, especially when 0.2 M reagent concentrations are employed.

TABLE 5

| Cycle # | N.L. (μmol/g) | A.Y. (%) | L.A. Amt. (mg) | Oligonucleotide Sequence | Oligo. Yield ($A_{260}$ units) |
|---|---|---|---|---|---|
| 1 | 39 | 97.5 | 180 | dGTAAAACGACGGCCAGT | 599 |
| 2 | 46 | 98.1 | 146 | dGATTTAGGTGACACTAT | 585 |
| 3 | 39 | 97.9 | 118 | dTGCCTAATGAGTGAGCT | 581 |

TABLE 6

| Cycle # | N.L. ($\mu$mol/g) | A.Y. (%) | L.A. Amt. (mg) | Oligonucleotide Sequence | Oligo. Yield ($A_{260}$ units) |
|---|---|---|---|---|---|
| 1 | 56 | 97.7 | 132 | dGTAAAACGACGGCCAGT | 723 |
| 2 | 66 | 97.6 | 125 | dCTTGGCGTAATCATGGT | 747 |
| 3 | 49 | 98.2 | 119 | dTGCCTAATGAGTGAGCT | 622 |
| 4 | 49 | 98.2 | 106 | dGTCGTGCCAGCTGCATT | 503 |
| 5 | 44 | 97.8 | ~100 | dCCGCTTCCTCGCTCACT | 378 |
| 6 | 40 | 97.0 | ~100 | dGTAAAACGACGGCCAGT | 275 |

TABLE 7

| Cycle # | B* | N.L. ($\mu$mol/g) | A.Y. (%) | Oligonucleotide Sequence | Oligo. Yield ($A_{260}$ units) |
|---|---|---|---|---|---|
| 1 | T | 64.7 | — | — | — |
| 2 | T | 53.5 | 98.2 | dGTAAAACGACGGCCAGT | 62 |
| 3 | $A^{Bz}$ | 33.1 | 98.8 | dGAGTCGACCTGCAGGCA | 41 |
| 4 | $C^{Bz}$ | 44.3 | 99.0 | dACATACGAGCCGGAAGC | 56 |
| 5 | $G^{iBu}$ | 13.9 | 99.2 | dTGCCCGCTTTCCAGTCG | 17 |

TABLE 8

| Example | B* | Conc. (M) | Coupling Agent[1] | 60 sec[3] | 150 sec[3] | 300 sec[3] | 600 sec[3] |
|---|---|---|---|---|---|---|---|
| 27 | $A^{Bz}$ | 0.05 | HBTU/DMAP | 7.2 | — | — | 22.9 |
| 28 | $A^{Bz}$ | 0.05 | HATU/DMAP | 8.5 | — | — | 30.0 |
| 29 | $A^{Bz}$ | 0.05 | HBTU/HOBT[2] | — | — | — | 4.7 |
| 30 | $A^{Bz}$ | 0.05 | HATU/HOAT[2] | — | — | — | 5.0 |
| 31 | $A^{Bz}$ | 0.2 | HBTU/HOBT[2] | — | — | — | 14.7 |
| 32 | $A^{Bz}$ | 0.2 | HBTU/DMAP | 26.3 | — | — | 66.0 |
| 33 | $A^{Bz}$ | 0.2 | HATU/DMAP | 38.9 | 54.3 | 75.7 | 89.2 |
| 34 | $C^{Bz}$ | 0.05 | HBTU/DMAP | — | — | — | 18.0 |
| 35 | $C^{Bz}$ | 0.05 | HATU/DMAP | — | — | — | 30.6 |
| 36 | $G^{iBu}$ | 0.05 | HBTU/DMAP | — | — | — | 19.0 |
| 37 | $G^{iBu}$ | 0.05 | HATU/DMAP | 9.4 | — | — | 32.9 |
| 38 | T | 0.05 | HBTU/DMAP | — | — | — | 10.9 |
| 39 | T | 0.05 | HATU/DMAP | — | — | — | 18.3 |

Notes:
[1] unless otherwise indicated all reagents are in a 1:1 molar ratio
[2] also includes one equivalent of DIEA.
[3] wait step

What is claimed is:

1. A solid support for oligonucleotide synthesis, the solid support having the following formula:

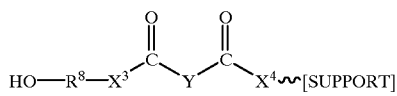

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or differed and are selected from the group consisting of —O—, —S—, —S(O)$_2$— and —N(R$^{12}$)—; $R^{12}$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; and Y is selected from the group consisting of:

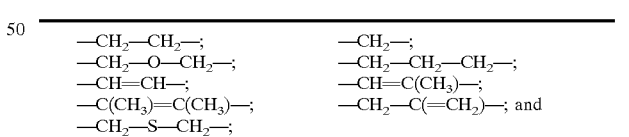

wherein when Y is —CH$_2$—CH$_2$—, at least one of $X^3$ and $X^4$ is —O—.

2. The solid support defined in claim 1, wherein $R^8$ is a substituted or unsubstituted $C_1$–$C_{20}$ alkyl group.

3. The solid support defined in claim 1, wherein Y is —CH$_2$—CH$_2$—.

4. The solid support defined in claim 1, wherein SUPPORT is an inorganic substance.

5. The solid support defined in claim 1, wherein SUPPORT is an organic substance.

6. A chemically modified solid support for oligonucleotide synthesis, the support having the formula:

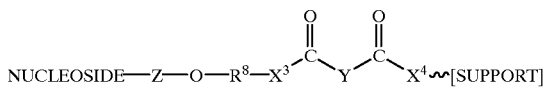

wherein:
R$^8$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
X$^3$ and X$^4$ are the same or different and each is selected from the group consisting of —O—, —S—, —S(O)$_2$— and —N(R$^{12}$)—;
R$^{12}$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
Y is selected from the group consisting of:

| | |
|---|---|
| —CH$_2$—CH$_2$—; | —CH$_2$—; |
| —CH$_2$—O—CH$_2$—; | —CH$_2$—CH$_2$—CH$_2$—; |
| —CH=CH—; | —CH=C(CH$_3$)—; |
| —C(CH$_3$)=C(CH$_3$)—; | —CH$_2$—C(=CH$_2$)—; and |
| —CH$_2$—S—CH$_2$—; | | and Z is a diradical linker moiety; wherein when Y is —CH$_2$—CH$_2$—, at least one of X$^3$ and X$^4$ is —O—.

7. The support defined in claim 6, wherein Z is a diradical linker moiety selected from the group consisting of:

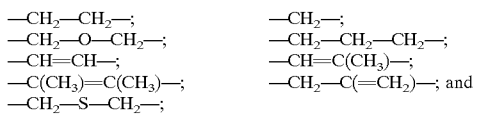

8. The support defined in claim 6, wherein Z is a diradical linker moiety having the formula:

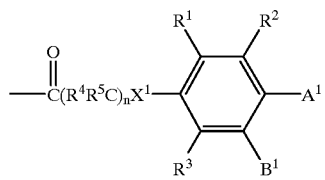

wherein:
R$^1$, R$^2$ and R$^3$ are the same or different and each is selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
R$^4$ and R$^5$ are the same or different and each is selected from the group consisting of hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
X$^1$ is selected from the group consisting of —O—, —S—, —C(O)—, —S(O)$_2$— and —N(R)—;
R is selected from the group consisting of hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
n is 0,1 or 2;
one of A$^1$ and B$^1$ is selected from the group consisting of hydrogen, halide, a substituted or unsubstituted C$_5$–C$_{20}$ alkyl group, a substituted or unsubstituted C$_1$–C$_{30}$ aryl group and a substituted or unsubstituted C$_5$–C$_{40}$ alkylaryl group,
the other of A$^1$ and B$^1$ has the formula:

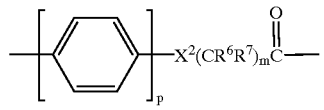

wherein:
p is 0 or 1;
X$^2$ is selected from the group consisting of —O—, —S—, —C(O)—, —S(O)$_2$— and —N(R)—;
R is selected from the group consisting of hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group,
R$^6$ and R$^7$ are the same or different and each is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
m is 0,1 or 2.

9. The support defined in claim 8, wherein B$^1$ is selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group.

10. The support defined in claim 8, wherein each of R$^4$, R$^5$, R$^6$ and R$^7$ is hydrogen.

11. The support defined in claim 8, wherein each of m and n are 1.

12. The support defined in claim 8, wherein each of R$^1$, R$^2$ and R$^3$ is hydrogen.

13. The support defined in claim 8, wherein X$^1$ and X$^2$ are both —O—.

14. The support defined in claim 6, wherein R$^8$ is a substituted or unsubstituted C$_1$–C$_{20}$ alkyl group.

15. The support defined in claim 6, wherein Z is a diradical linker moiety having the formula:

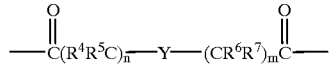

wherein:
R$^4$, R$^5$, R$^6$ and R$^7$ are the same or different and each is selected from the group consisting of hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;
Y is selected from the group consisting of —O—, —S—, —S(O)$_2$ and —O—((CH$_2$)$_L$—O)$_q$—;
L is an integer less than or equal to 60;
q is an integer in the range of 1–1000; and
n and m are the same or different and each is 0, 1 or 2;
with the proviso that, when Y is O, at least one of n and m is 2.

16. The support defined in claim 6, wherein Y is —CH$_2$—CH$_2$—.

17. The support defined in clam 6, wherein NUCLEOSIDE is a moiety selected from the group consisting of:

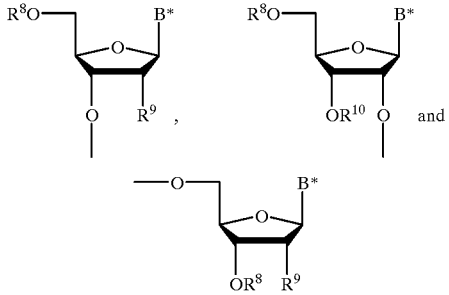

wherein:

$R^8$ and $R^{10}$ are the same or different and each is hydrogen or a protecting group;

$R^9$ is hydrogen or —OR$^{11}$;

$R^{11}$ is hydrogen or a protecting group; and

B* a nucleic acid base.

18. A process for production of a chemically modified solid support for oligonucleotide synthesis, the solid support having the formula:

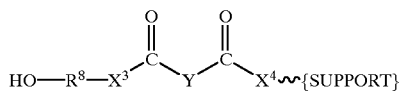

wherein:

$R^8$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;

$X^3$ and $X^4$ are the same or differed and each is selected from the group consisting of —O—, —S—, —S(O)$_2$— and —N(R$^{12}$)—;

$R^{12}$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;

Y is selected from the group consisting of:

| 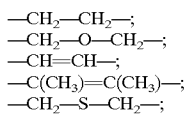 | 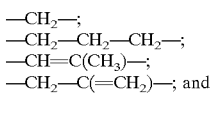 |
|---|---| wherein when Y is —CH$_2$–CH$_2$—, at least one of $X^3$ and $X^4$ is —O—;

the process comprising the steps of:
reacting a compound of Formula II with one of a compound of Formula I and a compound Formula III to form a conjugate; and
reacting the conjugate with the other of the compound of Formula I and the compound of Formula III;
the compounds of Formulae I, II and III having the following structures:

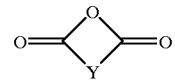
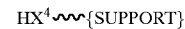

wherein $R^8$, $X^3$, $X^4$ and Y are as defined above.

19. The process defined in claim 18, wherein the compounds of Formulae I and II are initially reacted to form a conjugate which is reacted with the compound of Formula III.

20. The process defined in claim 18, wherein compounds of Formulae II and III are initially reacted to form a conjugate which is reacted with the compound of Formula I.

21. The process defined in claim 18, wherein $R^8$ is a substituted or unsubstituted C$_1$–C$_{20}$ alkyl group.

22. The process defined in claim 18, wherein Y is —CH$_2$—CH$_2$—.

23. The process defined in claim 18, wherein SUPPORT is an inorganic substance.

24. The process defined in claim 18, wherein SUPPORT is an organic substance.

25. A process for producing a chemically modified solid support for oligonucleotide synthesis, the support having the formula:

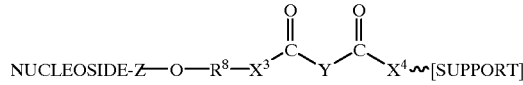

wherein:

$R^8$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;

$X^3$ and $X^4$ are the same or different and are selected from the group consisting of —O—, —S—, —S(O)$_2$— and N(R$^{12}$)—;

$R^{12}$ is selected from the group consisting of a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group;

Y is selected from the group consisting of:

| 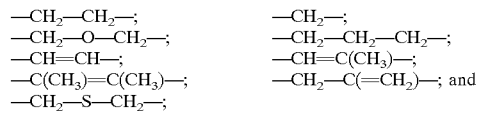 | 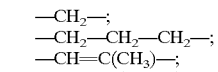 |
|---|---| and Z is a diradical linker moiety; wherein when Y is —CH$_2$—CH$_2$—, at least one of $X^3$ and $X^4$ is —O—;

the process comprising the steps of:
reacting a compound of Formula V with one of a compound of Formula IV and a compound Formula VI to form a conjugate having an ester linkage or an amide linkage therebetween; and
reacting the conjugate with the other of the compound of Formula IV and the compound of Formula VI to form an ester linkage or an amide linkage therebetween, the compounds of Formulae IV, V and VT having the following structures: NUCLEOSIDE-OH (IV) HO—Z—OH (V)

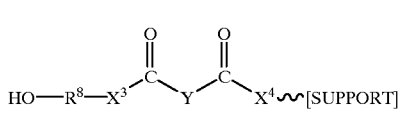

(VI)

wherein $R^8$, $X^3$, $X^4$, Y and Z are as defined above.

26. The process defined in claim 25, wherein the compounds of Formulae IV and V are initially reacted to form a conjugate which is reacted with the compound of Formula VI.

27. The process defined in claim 25, wherein compounds of Formulae V and VI are initially reacted to form a conjugate which is reacted with the compound of Formula IV.

28. The process defined in claim 25, wherein $R^8$ is a substituted or unsubstituted $C_1$–$C_{20}$ alkyl group.

29. The process defined in claim 25, wherein Y is —$CH_2$—$CH_2$—.

30. The process defined in claim 25, wherein each of $R^4$, $R^5$, $R^6$ and $R^7$ is hydrogen.

31. The process defined in claim 25, wherein each of m and n is 1.

32. The process defined in claim 25, wherein each of $R^1$, $R^2$ and $R^3$ is hydrogen.

33. The process defined in claim 25, wherein $X^1$ and $X^2$ are both —O—.

34. The process defined in claim 25, wherein SUPPORT is an inorganic substance.

35. The process defined in claim 25, wherein SUPPORT is an organic substance.

36. The process defined in claim 25, wherein Z is a diradical linker moiety selected from the group consisting of:

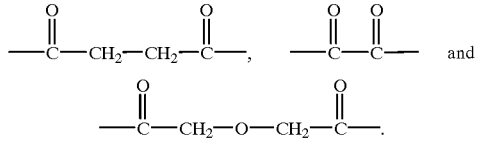

37. The process defined in claim 25, wherein Z is a diradical linker moiety having the formula:

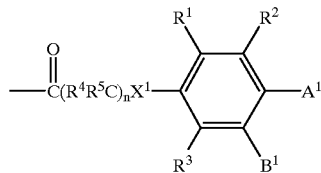

wherein:

$R^1$, $R^2$ and $R^3$ are the same or different and each is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

$R^4$ and $R^5$ are the same or different and each is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

$X^1$ is selected from the group consisting of —O—, —S—, —C(O)—, —S(O)$_2$— and —N(R)—;

R is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

n is 0, 1 or 2;

one of $A^1$ and $B^1$ is selected from the group consisting of hydrogen, halide, a substituted or unsubstituted $C_5$–$C_{20}$ alkyl group, a substituted or unsubstituted $C_1$–$C_{30}$ aryl group and a substituted or unsubstituted $C_5$–$C_{40}$ alkylaryl group, the other of $A^1$ and $B^1$ has the formula:

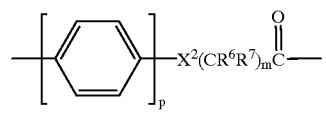

wherein:

p is 0 or 1;

$X^2$ is selected from the group consisting of —O—, —S—, —C(O)—, —S(O)$_2$— and —N(R)—;

R is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

$R^6$ and $R^7$ are the same or different and each is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

m is 0, 1 or 2.

38. The process defined in claim 37, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

39. The process defined in claim 25, wherein Z is a diradical linker moiety having the formula:

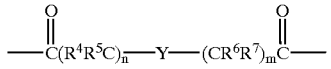

wherein:

$R^4$, $R^5$, $R^6$ and $R^7$ are the same or different and each is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group;

Y is selected from the group consisting of —O—, —S—, —S(O)$_2$ and —O—((CH$_2$)$_L$—O)$_q$—;

L is an integer less than or equal to 60;

q is an integer in the range of 1–1000; and n and m are the same or different and each is 0, 1 or 2; with the proviso that, when Y is O, at least one of n and m is 2.

40. The support defined in claim 25, wherein NUCLEOSIDE is a moiety selected from the group consisting of:

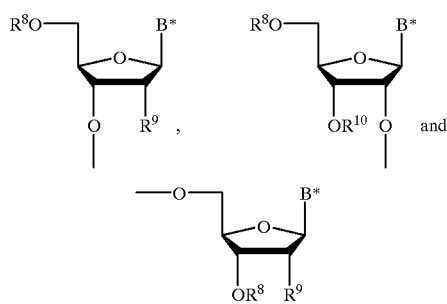
wherein:
R[8] and R[10] are the same or different and each is hydrogen or a protecting group;
R[9] is hydrogen or —OR[11];
R[11] is hydrogen or a protecting group; and
B* a nucleic acid base.
* * * * *